(12) United States Patent
Gunaratnam et al.

(10) Patent No.: US 6,491,034 B1
(45) Date of Patent: Dec. 10, 2002

(54) GAS DELIVERY CONNECTION ASSEMBLY

(75) Inventors: Michael K. Gunaratnam, Marsfield; Philip R. Kwok, Chatswood; Perry D. Lithgow, Glenwood, all of (AU)

(73) Assignee: ResMed Limited, North Ryde (AU)

( * ) Notice: Subject to any disclaimer, the term of this patent is extended or adjusted under 35 U.S.C. 154(b) by 0 days.

(21) Appl. No.: 09/498,705

(22) Filed: Feb. 7, 2000

(30) Foreign Application Priority Data

Feb. 9, 1999 (AU) .............................................. PP8550

(51) Int. Cl.[7] .............................................. A61M 16/00
(52) U.S. Cl. ........................... 128/204.18; 128/205.25; 128/206.15; 128/202.27; 128/912
(58) Field of Search ........................... 128/202.27, 912, 128/204.18, 206.12, 206.15, 206.16, 206.21, 206.26, 206.28, 207.12, 205.25; 285/305, 81, 86

(56) References Cited

U.S. PATENT DOCUMENTS

| | | | | |
|---|---|---|---|---|
| 3,824,999 A | * | 7/1974 | King ........................... 128/185 |
| 4,111,197 A | * | 9/1978 | Warncke et al. .......... 128/142.4 |
| 4,494,538 A | * | 1/1985 | Ansite ................... 128/205.25 |
| 4,506,665 A | * | 3/1985 | Andrews et al. ....... 128/202.27 |
| 4,580,556 A | * | 4/1986 | Kondur .................. 128/206.28 |
| 4,794,921 A | * | 1/1989 | Lindkvist ............... 128/203.29 |
| 4,807,617 A | * | 2/1989 | Nesti ...................... 128/205.12 |
| 4,841,953 A | * | 6/1989 | Dodrill .................. 128/202.27 |
| 4,875,714 A | * | 10/1989 | Lee .............................. 285/86 |
| 4,997,217 A | * | 3/1991 | Kunze ........................ 285/387 |
| 5,215,336 A | * | 6/1993 | Worthing ..................... 285/81 |
| 5,676,133 A | * | 10/1997 | Hickle et al. .......... 128/205.12 |
| 5,709,204 A | * | 1/1998 | Lester .................... 128/205.25 |
| 5,860,677 A | * | 1/1999 | Martins et al. ............... 285/26 |
| 5,937,851 A | * | 8/1999 | Serowski et al. ...... 128/202.27 |
| 6,192,886 B1 | * | 2/2001 | Rudolph ................ 128/207.13 |

* cited by examiner

Primary Examiner—John G. Weiss
Assistant Examiner—Mital Patel
(74) Attorney, Agent, or Firm—Pillsbury Winthrop LLP

(57) ABSTRACT

A patient gas delivery apparatus includes a gas flow generator, a gas delivery conduit and a patient mask. Connected in series between the conduit and the mask is an assembly formed in at least two interengaging parts that may form a housing for an anti-asphyxia valve or flow sensor. The assembly further includes a mating portion for connection to the mask, the arrangement being such that connection of the assembly to the mask prevents disengagement of the interengaging connection between the two parts of the assembly.

19 Claims, 3 Drawing Sheets

GAS DELIVERY CONNECTION ASSEMBLY

BACKGROUND OF THE INVENTION

This invention relates to improvements in patient gas delivery apparatus of the kind used in the analysis and treatment of respiratory disorders. The invention will be described with particular reference to patient gas delivery apparatus used in the treatment of respiratory disorders such as Obstructive Sleep Apnea (OSA) but it is not intended to be limited thereto.

Patient gas delivery apparatus of the kind having a mask worn by a patient and a gas delivery conduit attached to the mask, is commonly used in the analysis and treatment of respiratory disorders. The gas conduit delivers a gas under pressure to the patient. It is necessary that the gas conduit is detachable from the mask to facilitate cleaning Patient gas delivery apparatus typically includes at minimum, a gas delivery conduit and a nose or full face mask. In some cases it is a clinical requirement that additional components be included, such as means for $CO_2$ washout, for example, vents, anti-asphyxia valves and the like. In some cases, these additional components must be assembled in between the gas delivery conduit and the mask. Problems with prior art assemblies include:

(a) They may be inadvertently assembled without the additional components (b) They may be incorrectly assembled, for example, incorrectly aligned (c) During the course of treatment, the patient may inadvertently remove or dismantle the assembly and incorrectly reassemble it.

SUMMARY OF THE INVENTION

The present invention is directed towards solving or ameliorating one or more of these problems. The invention will be described with reference to a full face mask and an anti-asphyxia valve, though other forms of mask and additional components may be used.

In one form, the invention resides in a patient gas delivery apparatus including a mask adapted for communication with a patient's airways, a gas flow generator and gas delivery conduit means, further including an assembly connected in series between the conduit means and the masks, said assembly being formed in at least two parts connected by interengaging connecting means, said assembly further including means for connection to the mask, wherein connection of the assembly to the mask prevents disengagement of the interengaging connecting means such that said at least two parts of the assembly cannot separate whilst the assembly is connected to the mask.

In a further form of the invention, there is provided an assembly for connection in series between a gas delivery conduit means and a patient mask in a patient gas delivery apparatus, the assembly being formed in at least two parts connected by interengaging connecting means, said assembly further including means for connection to the mask, wherein connection of the assembly to the mask prevents disengagement of the interengaging connecting means such that said at least two parts of the assembly cannot separate whilst the assembly is connected to the mask.

Preferably, the means for connection to the mask includes locking means located on the inner side of the mask, that is in the region of the mask that lies adjacent the patient's face, such that the assembly cannot be disconnected from the mask until the mask has been substantially removed from the patient.

Preferably also, the interengaging means connecting the two parts of the assembly includes detent means on a first of the parts which releasably engage a second of the parts, the detents being held in an engaged position by the mask whilst the assembly is connected to the mask.

Desirably, the mask and conduit are not adapted for direct interconnection without the assembly.

In one preferred form of the invention, the assembly may form a housing for one or more internal components, for example a valve member or a flow sensor.

Further preferred embodiments of the invention will now be described by way of example only with reference to the accompanying drawings in which.

Figure 1:
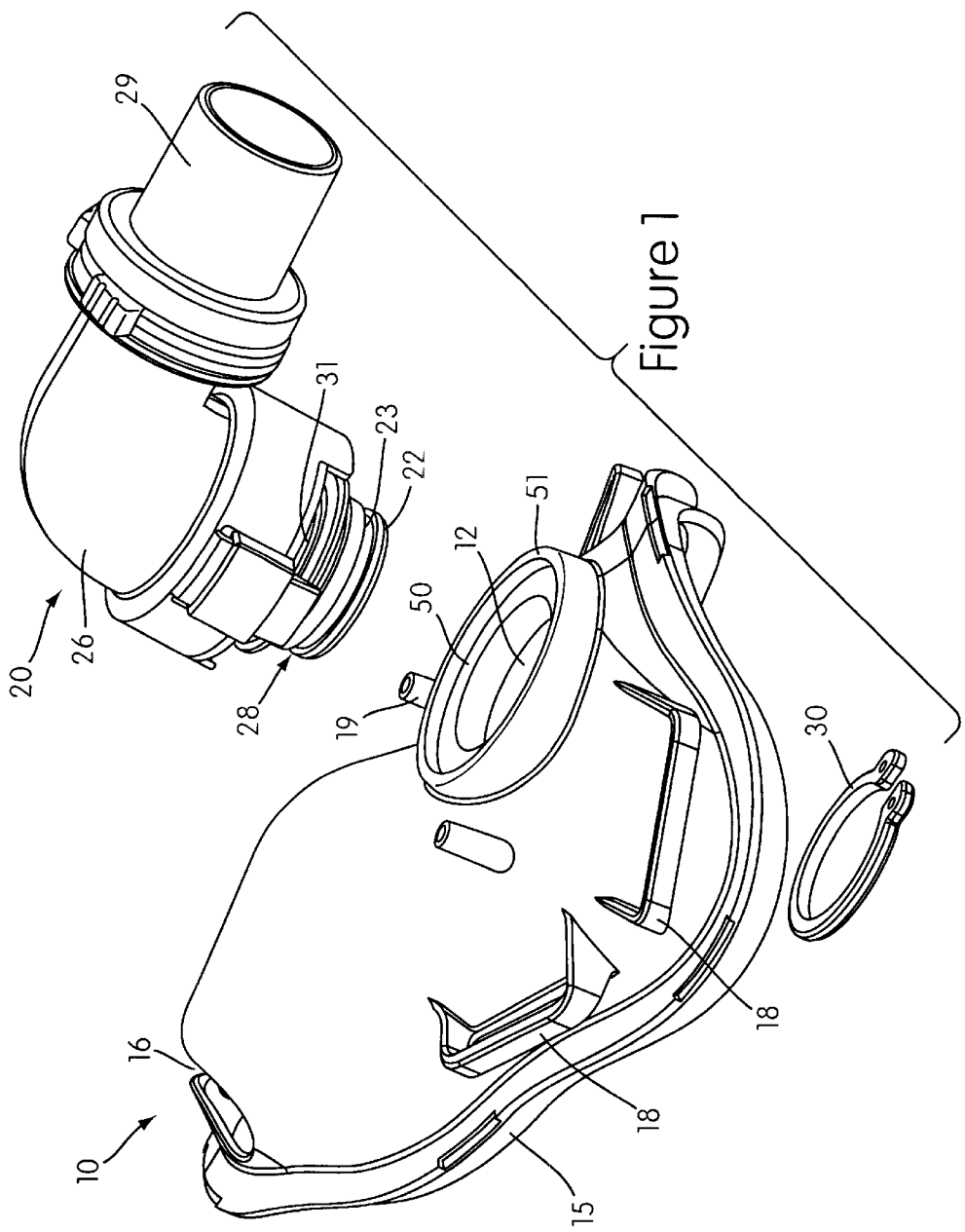
FIG. 1 is a perspective view showing the mask, anti-asphyxia valve housing and conduit connection assembly.

In FIG. 1 a mask frame is shown generally at 10. The mask is designed to be worn on a patient's face and is secured by means of straps (not shown) received by attachment points 18.

A conduit end assembly is shown generally at 20, including an elbow part 26 having at one end thereof a combined vent/connector piece 28. The elbow and vent/connector piece together form a housing for an anti-asphyxia valve or other internal components (not shown). At the other end of the elbow is a detachable swivel tube 29 for connection of the gas delivery conduit (not shown).

The mask 10 includes a circular aperture 12 sized to receive a mating portion 22 of the vent/connector piece 28. The mating portion 22 has an annular groove 23 formed therein that receives a locking means 30 in the form of a C-shaped clip attached after mating to the mask. The clip 30 has an outside diameter greater than the width of the aperture 12 and an inner diameter adapted to ensure a snug fit within the annular groove 23. The clip 30 is resilient and can expand sufficiently to allow the clip to be fitted into and removed from the groove 23. As shown in FIG. 1, the clip 30 is located onto the mating portion 22 on the inside of the mask 10. In this position, the clip 30 is inaccessible while the mask is being worn by a patient. Once the mating portion 22 of the vent/connector piece 28 has been inserted through the aperture 12 and the locking clip placed in the annular groove, the conduit end assembly 20 and the mask 10 cannot be separated without first removing the mask from the patient.

Figure 2:
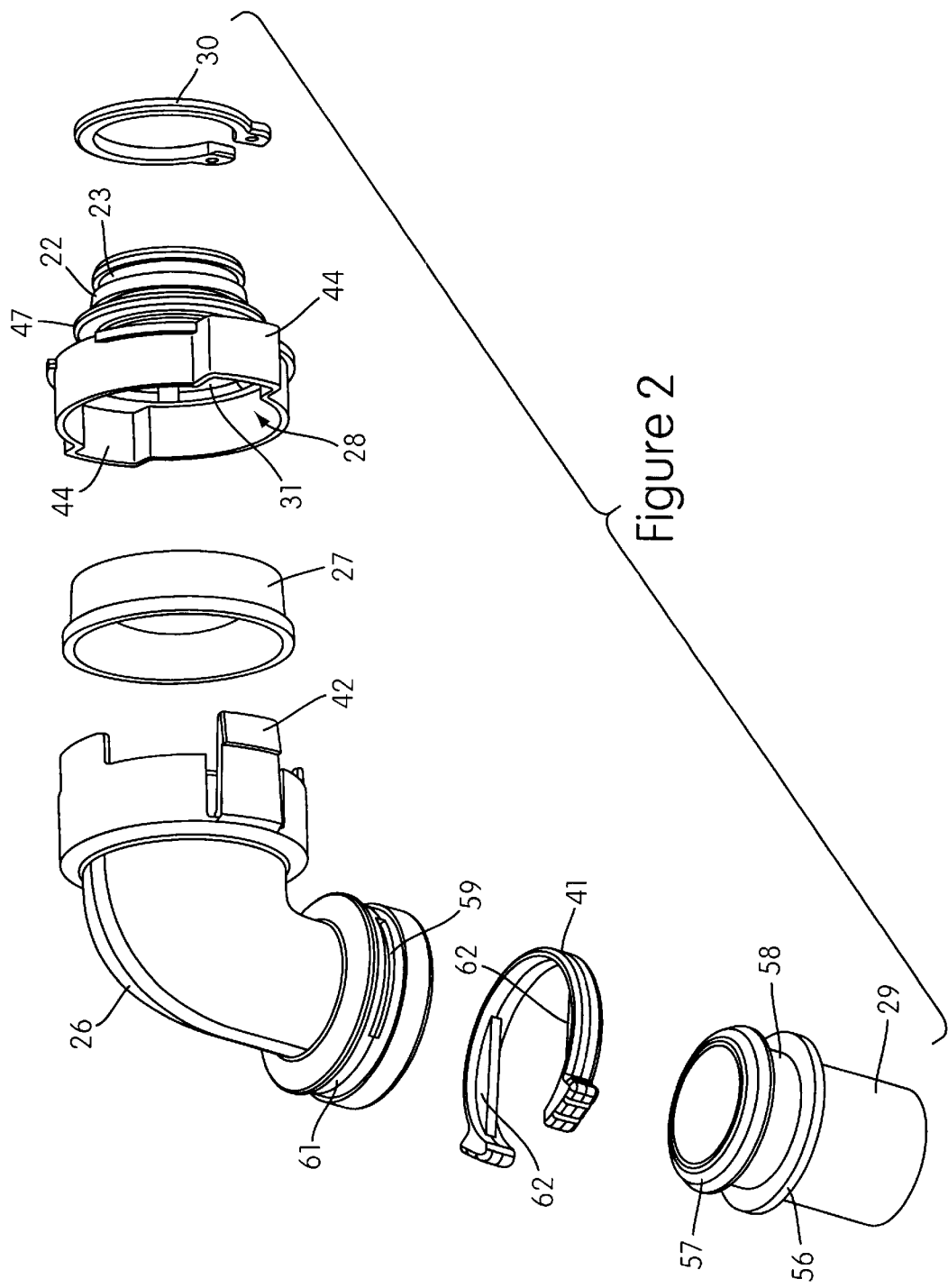
FIG. 2 is an exploded view of the anti-asphyxia valve and conduit connection assembly.

An exploded view of the anti-asphyxia valve and conduit connector assembly is shown in FIG. 2.

The end of the elbow 26 adjacent the mask 10 is fitted with an anti-asphyxia valve arrangement that provides an air passage to the patient in the event of failure of the gas delivery apparatus, consisting of a valve membrane 27 fitted into the end of elbow 26 and vents 31 in the vent/connector piece 28. During proper operation of the gas delivery system, the valve membrane remains in the orientation shown in FIG. 2, closing off the vents 31. In the event of a drop in pressure below a predetermined level, the valve membrane 27 flips to a reverse orientation, opening the vents 31. The consion and operation of the anti-asphyxia valve is described in more detail in the Applicant's Australian Patent Application No. 65527/99, the contents of which are incorporated herein by reference.

Resilient detents 42 on the elbow 26 pass through and engage behind slot-forming formations 44 in the vent/connector piece 28 to provide releasable engagement of the two parts.

The vent/connector piece has a collar 47 that abuts a corresponding surface of the mask 10 to limit the distance that the vent/connector piece can be inserted into the mask aperture 12 (FIG. 1). The corresponding surface is an annulus 50 having a protruding rim 51 the outer circumference of which preferably engages the inner surface of the detents 42 on insertion of the mating portion 22 into the aperture 12. This engagement prevents the detents from being pushed radially inwards sufficiently for the detents to disengage from behind the slot-forming formations 44, thus preventing the elbow 26 and vent/connector piece 28 from separating whilst still attached to the mask frame 11, for example during patient treatment. The result of this is the anti-asphyxia valve arrangement cannot be disassembled without first removing the elbow and vent/connector piece assembly from the mask. However, once disconnected from the mask, the assembly may be readily separated for cleaning and then reassembled.

The other, distal end of elbow 26 has an enlarged diameter portion which receives the swivel tube 29, onto which a flexible gas conduit (not shown) may be fitted. The swivel tube 29 has a pair of flanges 56 and 57 defining an annular groove 58 therebetween. The end of swivel tube 29 is inserted into the elbow 26 until the end flange 57 abuts an inner surface (not shown) within elbow 26. In this position the annular groove 58 is at least partially aligned with an annular groove 61 in the exterior of the elbow, which receives a swivel clip 41.

The swivel clip 41 has an inner diameter only slightly greater than the diameter of the groove 61, to ensure a snug fit within the groove. The clip 41 is resilient to permit sufficient expansion for attachment and removal of the clip from the groove. The groove 61 has slots 59 which receive lugs 62 on the clip. These lugs rotatably engage in the groove 58 between flanges 56 and 57 of the swivel tube. The swivel tube arrangement thus acts as a rotatable coupling between the conduit and the elbow whilst allowing quick attachment and removal of the gas conduit from the elbow regardless of whether the assembly is attached to the mask at the time.

Figure 3:
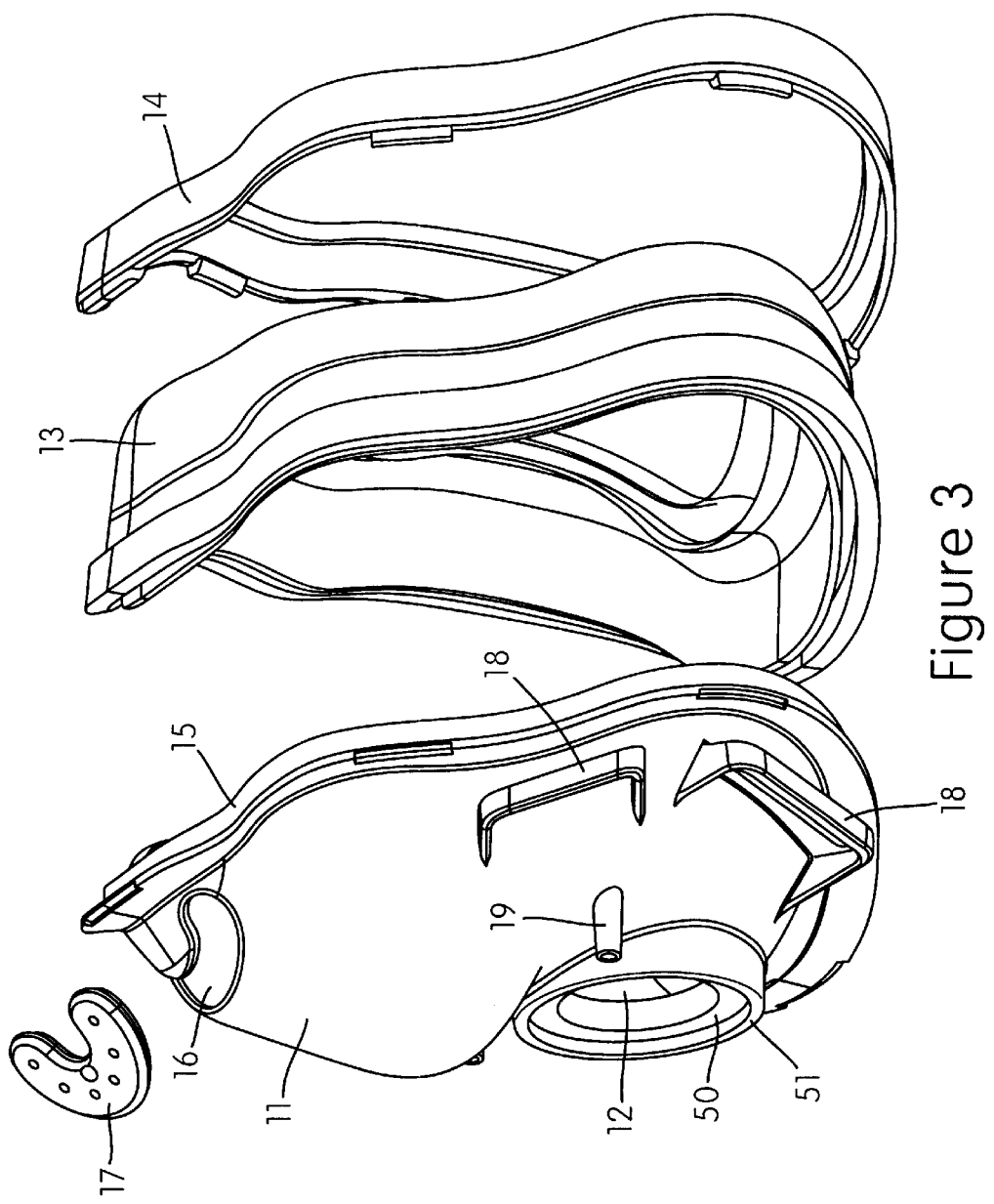
FIG. 3 is an exploded view of the mask assembly.

As shown in FIG. 3, the mask includes a mask frame 11, cushion 13 and cushion clip 14. The cushion is received on a rib 15 extending around the periphery of the mask frame 11. The cushion is held to the rib by the cushion clip 14. The mask frame includes attachment points 18 that receive straps (not shown) for attaching the mask to the patient, an aperture 16 for receiving an air vent 17, and measurement ports 19.

While particular embodiments of this invention have been described, it will be evident to those skilled in the art that the present invention may be embodied in other specific forms without departing from the essential characteristics thereof. The present embodiments and examples are therefore to be considered in all respects as illustrative and not restrictive, the scope of the invention being indicated by the appended claims rather than the foregoing description, and all changes which come within the meaning and range of equivalency of the claims are therefore intended to be embraced therein.

What is claimed is:

1. A patient gas delivery apparatus including:
a mask adapted for communication with a patient's airway;
a gas flow generator and a gas delivery conduit; and
an assembly connected in series between the conduit and the mask, said assembly being formed in at least two parts connected by interengaging connecting means, said assembly further including means for connection to the mask such that, by virtue of connecting the assembly to the mask, disengagement of the interengaging connecting means is prevented and said at least two parts of the assembly cannot separate whilst the assembly is connected to the mask.

2. The patient gas delivery apparatus according to claim 1, wherein said interengaging connecting means includes a detent on a first of said parts of the assembly, said detent releasably engaging a second of said parts of the assembly and being held in an engaged position by the mask whilst the assembly is connected to the mask.

3. The patient gas delivery apparatus according to claim 2, wherein said first and second parts form a housing for a flow sensor of said apparatus.

4. The patient gas delivery apparatus according to claim 2, wherein said first and second parts form a housing for an anti-asphyxia valve member.

5. The patient gas delivery apparatus according to claim 4, wherein said housing has at least one vent that is closed by said valve member during normal operation of said apparatus, and opened when pressure falls below a predetermined pressure.

6. The patient gas delivery apparatus according to claim 2, wherein said second part includes said means for connection of the assembly to the mask.

7. The patient gas delivery apparatus according to claim 6, wherein said means for connection to the mask includes a mating portion for insertion into an aperture of the mask and a lock attachable to said mating portion from an inner side of the mask so as to prevent withdrawal of the mating portion from said aperture, said detent being prevented from disengagement from said second part whilst said mating portion is inserted in said aperture.

8. The patient gas delivery apparatus according to claim 7, wherein said detent is prevented from said disengagement by contact with the mask.

9. The patient gas delivery apparatus according to claim 8, wherein the detent is resiliently biased in a radial direction relative to a common axis of said aperture and said mating portion such that the detent engages behind a respective formation on said second part, and wherein opposite radial movement of said detent to disengage from said second part is prevented by said contact.

10. The patient gas delivery apparatus according to claim 1, wherein a distal end of the assembly includes a rotatable coupling for connection of the conduit.

11. The patient gas delivery apparatus according to claim 10, wherein the mask and the conduit are not adapted for direct interconnection without the assembly.

12. A patient gas delivery apparatus including:
a mask adapted for communication with a patient's airway;
a gas flow generator and a gas delivery conduit; and
an assembly connected in series between the conduit and the mask, said assembly being formed in at least two parts connected by interengaging connecting means, said assembly further including means for connection to the mask such that, by virtue of connecting the assembly to the mask, disengagement of the interengaging connecting means is prevented and said at least two parts of the assembly cannot separate whilst the assembly is connected to the mask;
wherein said interengaging connecting means includes a detent on a first of said parts of the assembly, said detent releasably engaging a second of said parts of the assembly and being held in an engaged position by the mask whilst the assembly is connected to the mask;

wherein said second part includes said means for connection of the assembly to the mask;

wherein said means for connection to the mask includes a mating portion for insertion into an aperture of the mask and a lock attachable to said mating portion from an inner side of the mask so as to prevent withdrawal of the mating portion from said aperture, said detent being prevented from disengagement from said second part whilst said mating portion is inserted in said aperture;

wherein said detent is prevented from said disengagement by contact with the mask;

wherein the detent is resiliently biased in a radial direction relative to a common axis of said aperture and said mating portion such that the detent engages behind a respective formation on said second part, and wherein opposite radial movement of said detent to disengage from said second part is prevented by said contact; and wherein said disengagement is prevented by a projection on the mask.

13. The patient gas delivery apparatus according to claim 12, wherein said projection includes a projecting rim surrounding said aperture.

14. A patient gas delivery apparatus including:

a mask adapted for communication with a patient's airway;

a gas flow generator and a gas delivery conduit; and an assembly connected in series between the conduit and the mask, said assembly being formed in at least two parts connected by interengaging connecting means, said assembly further including means for connection to the mask such that, by virtue of connecting the assembly to the mask, disengagement of the interengaging connecting means is prevented and said at least two parts of the assembly cannot separate whilst the assembly is connected to the mask;

wherein said means for connection of the assembly to the mask includes a lock located on an inner side of said mask, such that substantial removal of the mask from the patient is a prerequisite for disconnection of the assembly from the mask and disengagement of said interengagement means.

15. An assembly adapted for connection in series between a gas delivery conduit and a patient mask in a patient gas delivery apparatus, the assembly comprising:

at least two parts connected by interengaging connecting means; and means for connection to the mask such that, by virtue of connecting the assembly to the mask, disengagement of the interengaging connecting means is prevented, and such that said at least two parts of the assembly cannot separate whilst the assembly is connected to the mask.

16. The assembly according to claim 15, further including an anti-asphyxia valve member housed in said assembly.

17. The assembly according to claim 16 wherein said assembly has at least one vent, said valve member being adapted to close said vent during normal operation of the apparatus and to open when pressure falls below a predetermined pressure.

18. A patient gas delivery apparatus including:

a mask adapted for communication with a patient's airway;

a gas flow generator and a gas delivery conduit associated with the mask; and an assembly connected in series between the conduit and the mask, said assembly being formed in at least two parts connected by an interengagement connector, said assembly being connected to the mask such that a portion of the mask prevents disengagement of the interengagement connector and said at least two parts of the assembly cannot separate whilst the assembly is connected to the mask.

19. A patient gas delivery apparatus including:

a mask adapted for communication with a patient's airway;

a gas flow generator and a gas delivery conduit associated with the mask; and an assembly connected in series between the conduit and the mask, said assembly being formed in at least two interconnected parts, at least one of said at least two parts being connected to the mask in such a manner that a portion of the mask prevents disengagement of the at least two parts from one another whilst the assembly is connected to the mask.

* * * * *